(12) United States Patent
Zimmerman (10) Patent No.: US 12,099,554 B2
(45) Date of Patent: Sep. 24, 2024

(54) SYSTEM AND METHOD FOR PERFORMING FAST STATISTICAL PATTERN HINTS DETECTION

(71) Applicant: DaBoost Systems LTD., Gan Yavne (IL)

(72) Inventor: Israel Zimmerman, Gan Yavne (IL)

(73) Assignee: DaBoost Systems LTD., Gan Yavne (IL)

( * ) Notice: Subject to any disclaimer, the term of this patent is extended or adjusted under 35 U.S.C. 154(b) by 0 days.

(21) Appl. No.: 18/477,849

(22) Filed: Sep. 29, 2023

(65) Prior Publication Data

US 2024/0111813 A1    Apr. 4, 2024

Related U.S. Application Data

(63) Continuation of application No. PCT/IL2022/050342, filed on Mar. 31, 2022.

(30) Foreign Application Priority Data

Apr. 1, 2021 (IL) .......................................... 281960

(51) Int. Cl.
*G06F 16/903* (2019.01)
*G06F 16/901* (2019.01)
*G16B 40/20* (2019.01)

(52) U.S. Cl.
CPC ...... *G06F 16/90344* (2019.01); *G06F 16/901* (2019.01); *G16B 40/20* (2019.02)

(58) Field of Classification Search
CPC . G06F 16/90344; G06F 16/901; G16B 40/20; G16B 20/20; H04L 63/1425
See application file for complete search history.

(56) References Cited

U.S. PATENT DOCUMENTS

2012/0197928 A1* 8/2012 Zhang ................ G06F 16/2471
707/769
2014/0324821 A1* 10/2014 Meiyyappan ..... G06F 16/24562
707/715

(Continued)

OTHER PUBLICATIONS

International Search Report and Written Opinion, Patent Cooperation Treaty Application No. PCT/IL2022/050342, Jun. 29, 2022, 11 pages.

*Primary Examiner* — Cam Y T Truong
(74) *Attorney, Agent, or Firm* — Fenwick & West LLP; Daniel Brownstone (57) ABSTRACT

A system for performing fast data pattern searches, comprising a computerized device consisting of at least one processor and associated memory, which are adapted to automatically create condensed elementary units to be used, based on the data patterns or based on known elementary unit data; create an indexed dictionary containing the data patterns to be searched; select a primary key for each pattern using the statistics and secondary keys counting on the primary key value, the dictionary having entries that are balanced over all array entries, based on the numbers of the secondary keys; for each searched pattern, select a primary key to search for a first fragment of the searched pattern to be compared; create a secondary key to search for a second fragment of the searched pattern, the secondary key being greater that the size of the primary key to both directions, the secondary key functions as a filtering element, where only entries for which there is a match in the secondary key value and the corresponding distance will move to the next processing stage; process typical search data, based on the condensed elementary units and preforming a training stage to thereby obtain the fastest optimal combination on a primary key size and a secondary key size, to gather statistics regarding the probability of identifying data pat- (Continued)

terns; revoke entries options that are used more often according to a predetermined threshold; create third multiple keys for multiple fragments of the searched pattern, to be compared, and if there were matches, performing full comparison; at least one register for performing full or partial comparisons. The distance of the secondary key before or after the primary key is predetermined and wherein each entry of the array defines multiple entries to be compared as secondary keys, each one of the secondary keys with its unique defined distance from the primary key.

41 Claims, 8 Drawing Sheets

(56) References Cited

U.S. PATENT DOCUMENTS

| | | |
|---|---|---|
| 2015/0039614 A1 | 2/2015 | Daly et al. |
| 2017/0031981 A1* | 2/2017 | Leverich ........... G06F 16/24564 |
| 2017/0116370 A1 | 4/2017 | Doerr et al. |
| 2018/0157712 A1 | 6/2018 | Vestgote |

* cited by examiner

Dictionary = {Python, Java, J2ee, Ruby}

| 1 Caseless Nucleic Acid Code | 2 Meaning | 3 DNA - 4 Bit (Binary) | 4 RNA - 5 Bit (Binary) | 5 Proteins - 6 Bit (Binary) |
|---|---|---|---|---|
| A | A | 0001 | 00001 | 000001 |
| C | C | 0010 | 00010 | 000010 |
| G | G | 0100 | 00100 | 000100 |
| T | T | 1000 | 01000 | 001000 |
| U | U | | 10000 | 010000 |
| (i) | i | | | 100000 |
| R | A or G (i) | 0101 | 00101 | 100101 |
| Y | C, T or U | 1010 | 11010 | 011010 |
| K | G, T or U | 1100 | 11100 | 011100 |
| M | A or C | 0011 | 00011 | 000011 |
| S | C or G | 0110 | 00110 | 000110 |
| W | A, T or U | 1001 | 11001 | 011001 |
| B | not A (i.e. C, G, T or U) | 1110 | 11110 | 011110 |
| D | not C (i.e. A, G, T or U) | 1101 | 11101 | 011101 |
| H | not G (i.e. A, C, T or U) | 1011 | 11011 | 011011 |
| V | neither T nor U (i.e. A, C or G) | 0111 | 00111 | 000111 |
| N | A C G T U | 1111 | 11111 | 011111 |
| | | | | |
| Key Size: | | 24 Bits | 25 Bits | 24 Bits |
| Dictionary Entries | | 6 Nucleic | 5 Nucleic | 4 Nucleic |
| | | 2^24 | 2^25 | 2^24 |
| | | 16M Entries | 32M Entries | 16M Entries |

Fig. 7

SYSTEM AND METHOD FOR PERFORMING FAST STATISTICAL PATTERN HINTS DETECTION

FIELD OF THE INVENTION

The present invention relates to the field of fast data sequencing. More particularly, the present invention relates to a system and method for performing fast data multi-pattern searches, based on statistical pattern hints detection.

BACKGROUND OF THE INVENTION

Many fields of technology require fast searches of a large amount of patterns, simultaneously. For example, in cyber security and computational security, strings that are typical to viruses and other types of malware must be detected and classified very fast, in order to protect computers, servers and data networks and allow reacting to cyber-attacks, as quick as possible, in order to minimize potential damages.

Another example taken from the biology and bioinformatics (an interdisciplinary field that develops methods and software tools for understanding biological data, in particular when the data sets are large and complex) fields is DeoxyriboNucleic Acid (DNA) sequencing. Sequencing DNA means determining the order of the four chemical building blocks—called "bases"—that constitute the DNA molecule. The sequence tells scientists the kind of genetic information that is carried in a particular DNA segment. For example, scientists can use sequence information to determine which stretches of DNA contain genes and which stretches carry regulatory instructions, for turning genes on and off (i.e., gene activation and gene silencing). In addition, and importantly, sequence data can highlight changes in a gene that may cause diseases. Another type of sequencing is of Ribonucleic Acid (RNA—is a polymeric molecule essential in various biological roles in coding, decoding, regulation and expression of genes).

In the DNA double helix, the four chemical bases always bond with the same partner to form "base pairs." Adenine (A) always pairs with thymine (T); cytosine (C) always pairs with guanine (G). This pairing is the basis for the mechanism by which DNA molecules are copied when cells divide, and the pairing also underlies the methods by which most DNA sequencing experiments are done. The human Genome (all genetic information of an organism that is encoded by the DNA) contains about 3 billion base pairs that spell out the instructions for making and maintaining a human being. The Genome has two opposing directions of sequencing, combined together as a single unique DNA of any Animal, Plant, Human, Virus, Bacteria, Fungus, circulating free DNA (cfDNA—degraded DNA fragments released to the blood plasma and used to describe various forms of DNA freely circulating in the bloodstream), etc.

The most advanced method of sequencing today is NGS—New Genome Sequencing (NGS) that divides the DNA into randomly selected small parts (fragments) and uses special instruments that simultaneously read multiple DNA parts into binary data. The next step is trying to use an algorithm to gather those parts to reconstruct the original DNA sequence.

Searching the DNA genes or mutations (alterations in the genetic material (the genome) of a cell of a living organism or of a virus that is more or less permanent and that can be transmitted to the cell's or the virus's descendants) is a complicated task, since the DNA basis can be replaced or pass insertions or deletions, or the complete gene is sometimes reversed, etc.

For a DNA search, it is possible to define all four basis 'A', 'T', 'C', 'G' as "elementary units" for a desired DNA search. Those four basis can be represented by two bits as elementary units condensed data but since it is a more complicated task, part of the gene represented by multiple options and different letters are used for that process and for DNA 4 bits are used for each basis, where each bit represents the 'A', 'T', 'C', 'G' elementary units. For RNA 5 bits will be used.

For a string search, for example, 5 bits (32 condensed elementary units) or 6 bits (64 condensed elementary units) may be used, depending on the required upper case with or without lower case, where for numbers only, it is possible to use only 4 bits (10 digits, '+', '−', '.', ','). If other characters exists on the searched data, those values will be replaced by a "don't care" value. Since in a DNA search only 4 basis exist, there is no need for a "don't care" value and the condensed elementary unit will use only 4 bits.

The streamed data of a DNA on different DNA file types uses ASCII representation (a 256 entries constant conversion table is used), in order to obtain "on-the-fly" conversion that is required to perform the desired search.

Most of the existing typical searches use 8 bit (ASCII or binary) or 16 bit of data (a Unicode standard—is a system for the interchange, processing, and display of the written texts of the diverse languages) that can also use on-the-fly conversion to perform the desired search.

Data condensing is very important, since it will use only the effective bits required for comparing.

Primary key, secondary key and multiple keys can compare more ASCII characters during one comparison. For example:

If 5 bits is used for condensing string search with a pattern of 6 characters, 30 bit comparison can be used, instead of 48 bits, with 37.5% saving.

By using 512 bit registers like those existing on modern CPUs, more than 100 characters can be inside of one register.

The impact is more dramatically applied on the CPU cache, since all the comparisons are done without memory paging, thereby increasing the search speed.

In case of a DNA search, the condensed 4 bits can store 256 basis on one register and the total of approximately 3 Giga basis of human genome, is reduced to 1500 Mbytes.

After sequencing, there is a need to rapidly search for particular genes and mutations having typical patterns. This technology is useful for creating compressed DNA files and for gene indexing, where all genes and mutations are searched within the genome itself.

By using known indexed dictionary for all genes and mutations, it is possible to store only the index and the difference for each gene and mutation, and all the unidentified parts. This method is able to compress the raw DNA to less than 10% of the original size.

The DNA search is considered to be an "Inaccurate" search, compared to a regular string search with "Accurate" binary pattern data. However, the task of searching very large patterns while increasing the required search patterns (such as malware patterns or genes and mutations) introduces a substantial challenge, especially when the search is made within streamed data.

Existing pattern search technologies such as Intel's Hyperscan (a high performance regular expression matching library) can find and detect about 20000-40000 patterns per second, while running on a server with more than 40 cores. However, while dealing with huge amounts of data (such as searching within a human Genome), fast detection techniques should be able to provide detection rates of hundreds of thousands of patterns, or even millions of patterns per second. Another challenge is the requirement for high detection accuracy, which is close to 100%.

These constrains of very fast detection rates and high detection accuracy, require complex and expensive computation hardware to increase processing power, such as powerful CPUs and a huge amount of buffers (to hold the searched data), where the size of each buffer must be at least the maximal length of a searched pattern.

Also, existing search methods are typically based on a predetermined dictionary, which comprises all the patterns to be searched, while performing a full comparison between words in the dictionary and segments of the streamed or stored data. However, this solution is complex and requires very high overhead in terms of processing power and memory resources.

Figure 1:
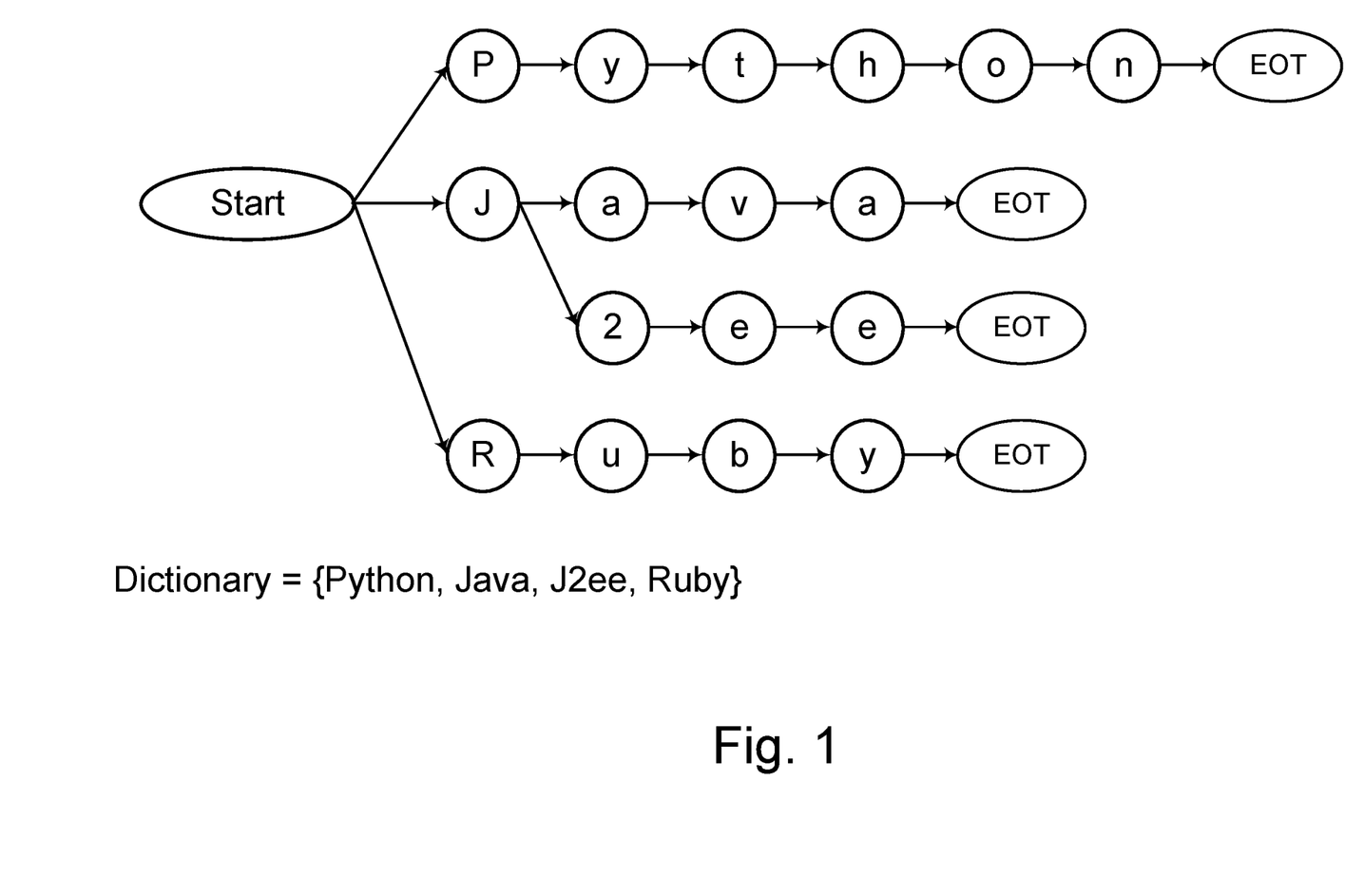
FIG. 1 (prior art) shows a typical existing solution for searching in a dictionary.

A typical existing solution for searching in a dictionary is shown in FIG. 1 (prior art). In this example, the dictionary comprises the words "Python", "Java", "J2ee" and "Ruby". Prior art searches seek full matching of a searched word or string to one of the stored dictionary. For example, a searching task may be to detect if the string "Python" (which is a search key) is in the dictionary. In this case, the key will be stored in a buffer of length 5 (5 ASCII letters) and a CPU will make a comparison of the entire key "Python" and find that this key is in the dictionary. However, this requires a large memory and long processing time, which do not allow fast reaching to a final result.

It is therefore an object of the present invention to provide a method for performing fast multiple data pattern searches simultaneously, with complete match.

It is another object of the present invention to provide a method for performing fast data pattern searches, which is very fast and requires substantially less CPU cycles.

It is a further object of the present invention to provide a method for performing fast data pattern searches, with direct access to streamed data.

Other objects and advantages of the invention will become apparent as the description proceeds.

SUMMARY OF THE INVENTION

A method for performing fast data pattern searches, comprising the steps of:
a) automatically or manually creating condensed elementary units to be used, based on the data patterns or based on known elementary unit data;
b) creating an indexed dictionary containing the data patterns to be searched;
selecting a primary key for each pattern using the statistics and secondary keys counting on the primary key value, the dictionary having entries that are balanced over all array entries, based on the numbers of the secondary keys.
c) for each searched pattern, selecting a primary key to search for a first fragment of the searched pattern to be compared;
d) creating a secondary key to search for a second fragment of the searched pattern, the secondary key being greater that the size of the primary key to both directions, the secondary key functions as a filtering element, where only entries for which there is a match in the secondary key value and the corresponding distance will move to the next processing stage; and
e) processing typical search data, based on the condensed elementary units and preforming a training stage to thereby obtain the fastest optimal combination on a primary key size and a secondary key size, to gather statistics regarding the probability of identifying data patterns;
f) revoking entries options that are used more often according to a predetermined threshold;
g) creating third multiple keys for multiple fragments of the searched pattern, to be compared, and if there were matches, performing full comparison, wherein the distance of the secondary key before or after the primary key is predetermined and each entry of the array defines multiple entries to be compared as secondary keys, each one of the secondary keys with its unique defined distance from the primary key.

for each step, a full identified pattern may be obtained, to thereby support a combination of versatile patterns consisting of very small patterns.

The small patterns may range from 2 elementary units up to condensed pattern size of 2 Gigabyte on the same dictionary.

The elementary unit data may include one of the following:
DNA data;
numbers;
strings.

The threshold may be entries options that are used more than double times from other entries.

In one aspect, the searched data may be effectively cached data.

Full comparisons to obtain the final result may be made after performing partial searches consisting of a combination of partial accurate and inaccurate searches, thereby filtering out entry values that are not possible.

Entry values that are used more often may be deliberately revoked by pre-processing typical data.

The dictionary may contain only entries that were not revoked or values that do not exists.

The dictionary may be adapted to:
add new entries;
update existing entries;
delete existing entries.

Whenever there is an insertion of a gene or mutation, the insertion may be directed to an input in the array that has been minimally used.

The dictionary may include one or more of the following:
a collection of all genes and known mutations for humans, animals, plants, viruses, bacteria and fungus,
circulating free DNA (cfDNA);
full genomes sequence for existing life including humans, animals, plants, viruses, bacteria and fungus, etc.

The data may be condensed by performing a simple on-the-fly conversion.

Small fragmented definite areas within a pattern may reduce the key size.

The secondary key may be located near the primary key.

The secondary key and its distance from primary key may function as filtering elements, such that only entries for which there is a match in the secondary key value and the corresponding distance will move forward to the next stage.

Whenever all the keys and distances are larger than the value size, the bit size may include several values for each key.

Each array entry may have multiple entries that comply the primary key, to be compared as secondary keys, while for each one of the secondary keys, a distance from the primary key is defined.

The primary key and the secondary key with the distance between them may be accurate for an inaccurate search.

The types of entries may include:
entry values that are not possible;
entry values that are used more often;
entry values with multiple secondary keys with unique distance.

A system for performing fast data pattern searches, comprising:
a) a computerized device consisting of at least one processor and associated memory, which are adapted to:
  a.1) automatically create condensed elementary units to be used, based on the data patterns or based on known elementary unit data;
  a.2) create an indexed dictionary containing the data patterns to be searched; selecting a primary key for each pattern using the statistics and secondary keys counting on the primary key value, the dictionary having entries that are balanced over all array entries, based on the numbers of the secondary keys.
  a.3) for each searched pattern, select a primary key to search for a first fragment of the searched pattern to be compared;
  a.4) create a secondary key to search fora second fragment of the searched pattern, the secondary key being greater that the size of the primary key to both directions, the secondary key functions as a filtering element, where only entries for which there is a match in the secondary key value and the corresponding distance will move to the next processing stage; and
  a.5) process typical search data, based on the condensed elementary units and preforming a training stage to thereby obtain the fastest optimal combination on a primary key size and a secondary key size, to gather statistics regarding the probability of identifying data patterns;
  a.6) revoke entries options that are used more often according to a predetermined threshold;
  a.7) create third multiple keys for multiple fragments of the searched pattern, to be compared, and if there were matches, performing full comparison;
b) at least one register for performing full or partial comparisons,
wherein the distance of the secondary key before or after the primary key is predetermined and wherein each entry of the array defines multiple entries to be compared as secondary keys, each one of the secondary keys with its unique defined distance from the primary key.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein.

DETAILED DESCRIPTION OF THE PRESENT INVENTION

The present invention provides a system and method for performing fast data pattern searches, which is very fast, accurate and requires substantially less CPU cycles, using effectively cached data and allows direct access to streamed data. The system comprises a computerized device that consists of at least one processor and associated memory, which are adapted to perform partial accurate and inaccurate searches that are made before reaching a stage of full comparisons, so as to obtain a final search result.

The present invention can be implemented for ethernet stream filtering, such as firewalls and also for Anti-Virus scan, using the novel pattern search method.

Other computer fields of this invention are NoSql database search, ASCII parsers (like: HTML, XML, JSON) etc., using TAGS search inserted into dictionary like: <HTML>, </HTML>. By identifying those known TAGS combined with search patterns, an easy results filtering algorithm can be implemented, that will dramatically reduce the time required for obtaining results.

Upon implementing NGS on very small DNA fragments, such as a virus (200 basis or less than known Genes or Mutations), an automatic dictionary and keys can be defined as a preliminary process. After reading those fragments (based on the statistics for keys value pairs for primary and secondary keys), by using those alternative patterns, the original DNA sequence tags can be gathered and reconstructed easily to the original sequence.

The proposed new method is based on a combination of partial accurate and inaccurate searches that are made before reaching a stage of full comparisons, to obtain the final result. These partial searches allow filtering out entry values that are not possible. Entry values that are used more often are deliberately revoked by pre-processing typical data, such as Human Genome for DNA.

Using statistical analysis of typical patterns (called here a Statistical Pattern Hints Detection method or the SPHD method), allows saving unnecessary processing which requires power and CPU overhead. According to an embodiment of the present invention, an optimal dictionary is prepared in order to comply with the SPHD method, as will be explained later on. Generally, an indexed dictionary with a structure that complies with SPHD method is created. The dictionary should be balanced, since it can contain only entries that were not revoked or values that do not exists. The dictionary can add new entries, update an existing entry and delete existing entries, while having the ability to support new reached knowledge into the same dictionary, such as new found genes or mutations, or new malware patterns, without rebuilding the dictionary again and again each time for new knowledge.

Each time there is an insertion of a gene or mutation, the gene or mutation is directed to an input in the array that has been minimally used. This allows generating a database that contains all genes and mutations of animals and plants, for which there is DNA sequencing.

The dictionary can include:
a collection of all genes and known mutations for humans, animals, plants, viruses, bacteria and fungus, circulating free DNA (cfDNA);
RNA;
Complex proteins;
full genomes sequence for existing life: humans, animals, plants, viruses, bacteria and fungus, etc.

On the other hand, customized reduced data entry units can be created for a specific case, such as the following example:

| Character | 2 | a | b | e | H | J | n | o | P | R | t | u | v | y | Don't care |
|---|---|---|---|---|---|---|---|---|---|---|---|---|---|---|---|
| ASCII Value (Hex) | 0x32 | 0x61 | 0x62 | 0x65 | 0x68 | 0x4A | 0x6E | 0x6F | 0x50 | 0x52 | 0x74 | 0x75 | 0x76 | 0x79 | — |
| Condensed Value (Hex) | 0x0 | 0x1 | 0x2 | 0x3 | 0x4 | 0x5 | 0x6 | 0x7 | 0x8 | 0x9 | 0xa | 0xb | 0xc | 0xd | 0xe or 0xf |

The words "Python", "Java", "J2ee" and "Ruby" consist of the following letters:
The characters that represent elementary units are:
'2', 'a', 'b', 'e', 'J', 'h', 'J', 'n', 'o', 'P', 'R', 't', 'u', 'y', 'y' (14 elementary units—so it is possible to use only 4 bits and the 15-16 indexes values can be "don't care" elementary unit).

The table above represents this condensed replacement values for each ASCII value, that are gathered automatically from the search words:
Python—is represented by 0x8da476 (i.e., 8=P|d=y|a=t|4=h|7=o|6=n from the condensed values table)
Java—is represented by 0x51c1
J2ee—is represented by 0x5033
Ruby—is represented by 0x9b2d For example, the searched sentence is "Is Python in sentence":

| i | S | ' | P | y | t | h | o | n | ' | | i | n | | s | e | n | t | e | N | c | e | ? | | i | s | | ' | J |
|---|---|---|---|---|---|---|---|---|---|---|---|---|---|---|---|---|---|---|---|---|---|---|---|---|---|---|---|---|
| f | F | f | f | 8 | d | a | 4 | 7 | 6 | f | f | f | 6 | f | f | 3 | 6 | a | 3 | 6 | f | 3 | f | f | f | f | f | 5 |
| a | V | a | ' | | i | n | | s | e | n | t | e | n | c | e | ? | . | . | . | | | | | | | | | |
| 1 | C | 1 | f | f | f | 6 | f | f | 3 | 6 | a | 3 | 6 | f | 3 | f | f | f | f | | | | | | | | | |

In the memory, the data should be LSB (Least Significant Bit) aligned, the first letter 'i' value will be on the least 4 bits and 's' value will be at higher 4 bits of memory.

The memory Hex Dump (a hexadecimal view of computer data, from memory or from a computer file or storage device. In a hex dump, each byte (8 bits) is represented as a two-digit hexadecimal number) result of condensing will be:

Ff ff d8 4a 67 ff 6f ff 63 3a f6 f3 ff ff 5f c1 f1 ff f6 3f a6 63 3f ff ff

If a primary key size of 16 bit is selected, the words "Java", "J2ee", "Ruby" can be detected immediately using the direct index array size: 65536, while only Python should have an extra continued comparison for one more byte: 0x76.

If a larger direct array size of 24 bit is selected, it will require more memory but the direct index array size will have 16,777,216 entries of 8 bits, since only 4 words values are needed.

However, a further action is not needed, since the words Java, J2ee,Ruby should be placed on several entries on this array.

The entries that will have the same values are (XX represent all 256 options values filled on the direct index array):
Python—represented by 0x8da476
Java—represented by 0x51c1XX
J2ee—represented by 0x5033XX
Ruby—represented by 0x9b2dXX If a desired search does not require an exact Upper case or Lower case, it is possible to use translation and put the same value for the same letter on Upper case or Lower case like: 'a', 'A' to be value 1.

By performing a simple on-the-fly conversion, the data is condensed and becomes more effective, based on this unique method.

All the dictionary patterns data are pre-prepared during dictionary preparation and stored as condensed data, based on the condensed elementary units that have been used. Therefore, condensing elementary unit data, based on all patterns elementary data being used, has a great impact on any search and especially on the proposed search algorithm.

The proposed algorithm uses basic simple methods that can be implemented easily by hardware or software or by full algorithm implementation developed on a Field-Programmable Gate Array (FPGA—is an integrated circuit designed to be configured by a customer or a designer after manufacturing) chip or a special Hyperscan Application-Specific Integrated Circuit (ASIC).

Condensing data on-the-fly and shifting right large register are also simple algorithms that can be implemented easily as intrinsic opcodes (the portion of a machine language instruction that specifies the operation to be performed) in any future CPU that will improve this algorithm implementation.

In order to implement the SPHD method, search optimized parameters to be used for pattern detection are defined at the first stage. At the next stage, three types of search key are defined: a primary key (used to search for an first fragment of the search pattern), a secondary key and third multiple keys. Those different keys can be of different size, depending on the patterns used. For example, small fragmented definite areas within a pattern can reduce the key size.

Keys Definition and Dictionary Preparation Guidelines:
1. The primary key size<=MIN(all dictionary pattern condensed size)—Preferred option
   If the primary key size>MIN(all dictionary pattern condensed size)—Multiple entries that cover all optional values on direct access array will point for the same pattern
2. If (primary key size+secondary key size)>(pattern condensed size) perform check immediately for those patterns only. Patterns that do not comply with this rule, will continue to the next level with the secondary key comparison.
3. If (primary key size+secondary key size+multiple keys size)>(pattern condensed size) perform check immediately for those patterns only. Patterns that do not comply with this rule will continue to next level with the multiple key comparison.
4. Primary key and secondary key are not limited to elementary unit steps. For example: if each elementary unit is 5 bits, then the primary key size can be 11 bit, based on 11 bit the direct array size is $2^{11}=2048$.

Hint detection is based on key that are less common as possible among the searched patterns or the pre-processed typical data, where a "hint" represents the probability for the existence of a particular searched pattern.

In a DNA search, the genes and mutations contain approximately between 10,000 elementary units, up to 120,000 elementary units (where 4 bits are required per elementary unit).

All key values are selected from a definite (as much as possible) pattern areas. In DNA genes and mutations, there are lots of patterns variants and some basis on the sequence can have multiple basis options, while others can have definite values.

The primary key size defines also the size of a direct access memory (array) of entries. For example, a primary key of 16 bits represents direct access array with $2^{16}=65536$ entries. The primary key can be also with 32 bits size with 4 Giga elements $2^{32}=4,294,967,296$. Even though this will require additional memory (to handle 32 bits), it will be more efficient.

The secondary key size will typically be greater than the size of the primary key and will be located near the primary key. The distance between the primary key and the secondary key may vary and may be before or after the primary key. For example, when seeking a pattern within a DNA sequence, the distance of the secondary key may be 14 bits (which represents 7 DNA basis) or less.

A preferred value for the secondary key may be 8, 16, 32 or 64 bits, since these values correspond to the registers that are used by the most powerful existing CPUs and this allows performing many computations in parallel.

The secondary key and its distance from primary key function as filtering elements, where only entries for which there is a match in the secondary key value and the corresponding distance will move forward to the next stage.

Since the Hyperscan algorithm can support small patterns and very large patterns, small patterns can be identified only by the primary key and/or the secondary key stage. In such cases, the detection of this pattern is known and the algorithm will continue also to other patterns to verify if several patterns are complying with the key.

Each array entry can have multiple entries that comply the primary key, to be compared as secondary keys. For each one of the secondary keys, different distance from the primary key is defined.

A collected group of those secondary keys values from each required distance are gathered into one large register (of 512 bit or 256 bit or 64 bit or 32 bit or 16 bit) for performing a multiple comparing command, like the assembly opcode that exists on Intel AVX512 (512-bit SIMD instruction set that Intel has introduced in processors) or ARM (Arm Ltd., Cambridge, UK) CPUs or Graphics Processing Units (GPUs), so as to perform a fast search and reduce the CPU cycles.

The primary key and the secondary key with the distance between them must be accurate even in case of an inaccurate search.

In case of a DNA search, multiple entries on dictionary will be inserted to statistically increase the detection success.

At the next stage, third multiple keys to be compared are defined, where keys may be, for example, 8 groups of 64 bits (8×64), 16 groups of 32 bits (16×32), 32 groups of 16 bits (32×16) or 64 groups of 8 bits (64×8). Since at this stage there are fingerprints for a very large number of entries (each key has a different distance from the primary key), it is possible to make comparisons for all groups at the same time and thereby, accelerate the computation rate. Typically, calculations during each stage may be completed within 9 CPU cycles, such that even without any matching, all three stages can be completed at most within 50 CPU cycles.

If there were matches, at the next stage, a full comparison must be performed only on large patterns that are not fully covered by the primary key and the secondary key.

By using a direct access array (data structures that have the capability of mapping records to their corresponding keys using arrays), typical data to be used is processed and entries that will not be used are determined (since these entries are statistically used more often) to accelerate the data stream processing.

There are several types of entries: The first type includes entry values that are not possible. The second type includes entry values that are used more often, which are deliberately revoked during pre-processing of statistical typical data, for achieving faster processing rate. The third type includes entry values with multiple secondary keys (with a unique distance), functioning as a filter to the next stage.

Figure 2:
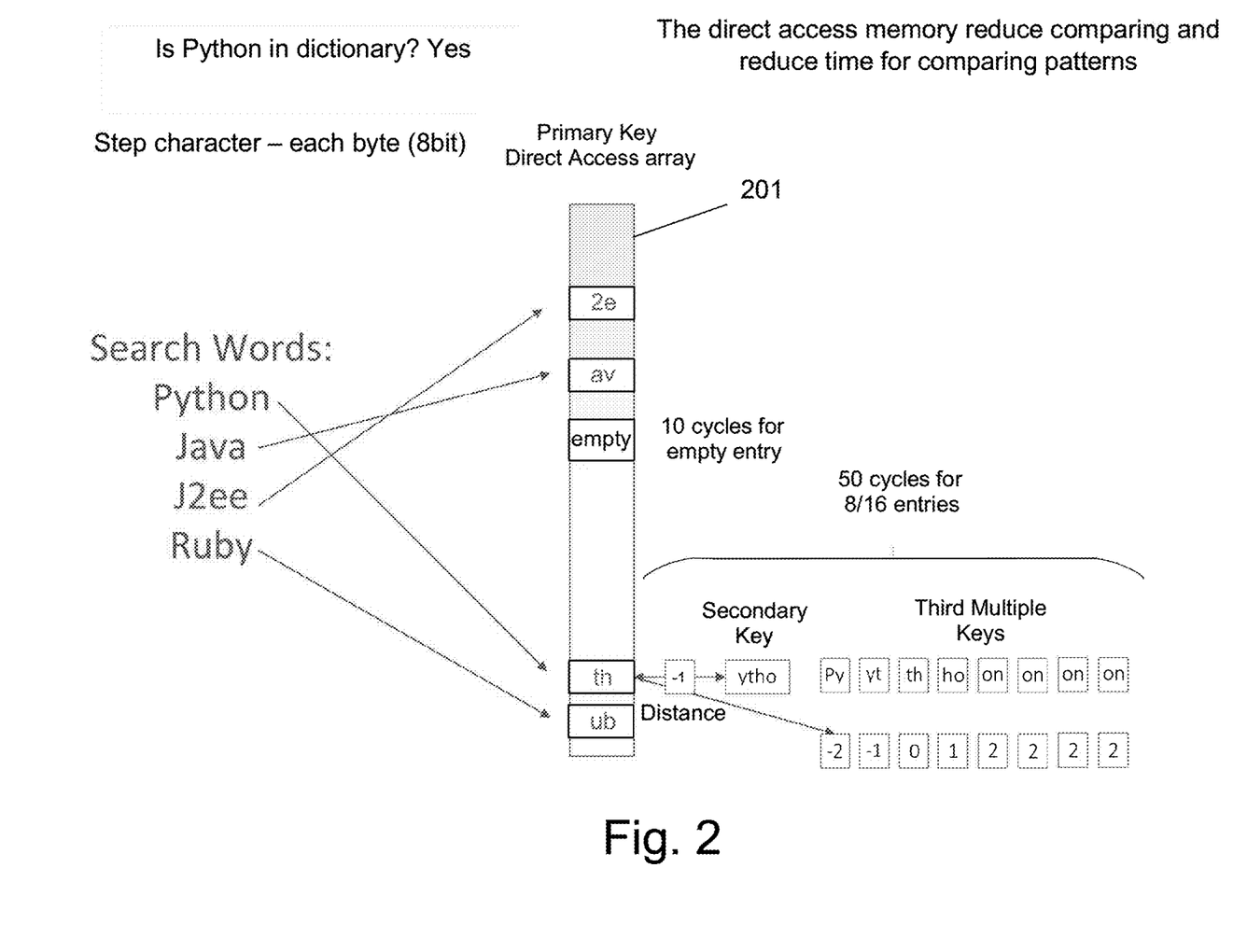
FIG. 2 illustrates an example for using the proposed keys, according to the invention.

An example for using the proposed keys (with uncondensed elementary data) is illustrated in FIG. 2. In this example, the word "Python" should be searched as the pattern (or string) to be detected in the dictionary. In this case, the primary key that is stored in the direct access array (memory which reduces the time needed to perform multiple comparisons) 201 is selected to be "th" (which is the pair of middle characters in the word "Python". At the next stage, the secondary key is selected to include 4 characters "ytho", resulting from keeping a distance of one character to the left (−1) and to the right (+1). At the next stage, the third multiple keys are selected to include 2 characters. In this example, the third keys are "Py", "yt", "th", "ho", "on", "on", "on", "on" resulting from selecting distances of two characters to the left (−2), one character to the left (−1), a zero character, one character to the right (+1), two characters to the right (+2), two characters to the right (+2), two characters to the right (+2) and two characters to the right (+2), respectively.

In this example, 50 CPU cycles were needed for an entry of 8 groups of 16 bits each.

After completing comparisons of the third stage multiple keys, there are several options to proceed:
Option 1:

For each entry that passed the comparison and found equal to one or more of the multiple keys comparison, the process continues to full comparison, with a unique function differently defined for each application.

Option 2:

Performing a binary function comparison for each byte. For unequal bytes, the process checks if it is a known Relative Virtual Address (RVA—in an image file, it is the address of an item after it is loaded into memory, with the base address of the image file subtracted from it) area.

Option 3:

Performing a partial comparison on "accurate" patterns and return as a negative result full negative comparison on all third level multiple keys as "inaccurate" patterns.

Option 4:

Performing a partial comparison on "inaccurate" patterns. Bioinformatics is more complicated because of "Deletion", "Insertion" and "Replacement" operations, which are more common in DNA sequences. In this option, the comparison should be done differently for each wing of the multiple keys by modifying steps to the right +/−entry unit steps, while trying to locate the displacement (due to insertion or deletion) between third multiple keys areas. After passing the third key comparison, all the information is transferred to a full comparison stage.

It should be indicated that during an "accurate" search, all the key values including the third multiple keys with their corresponding distances must be correct. On the other hand, during an "inaccurate" search, at least three elements must be correct. These elements are the primary key value, the distance between the primary key and the secondary key and the secondary key value.

Figure 3:
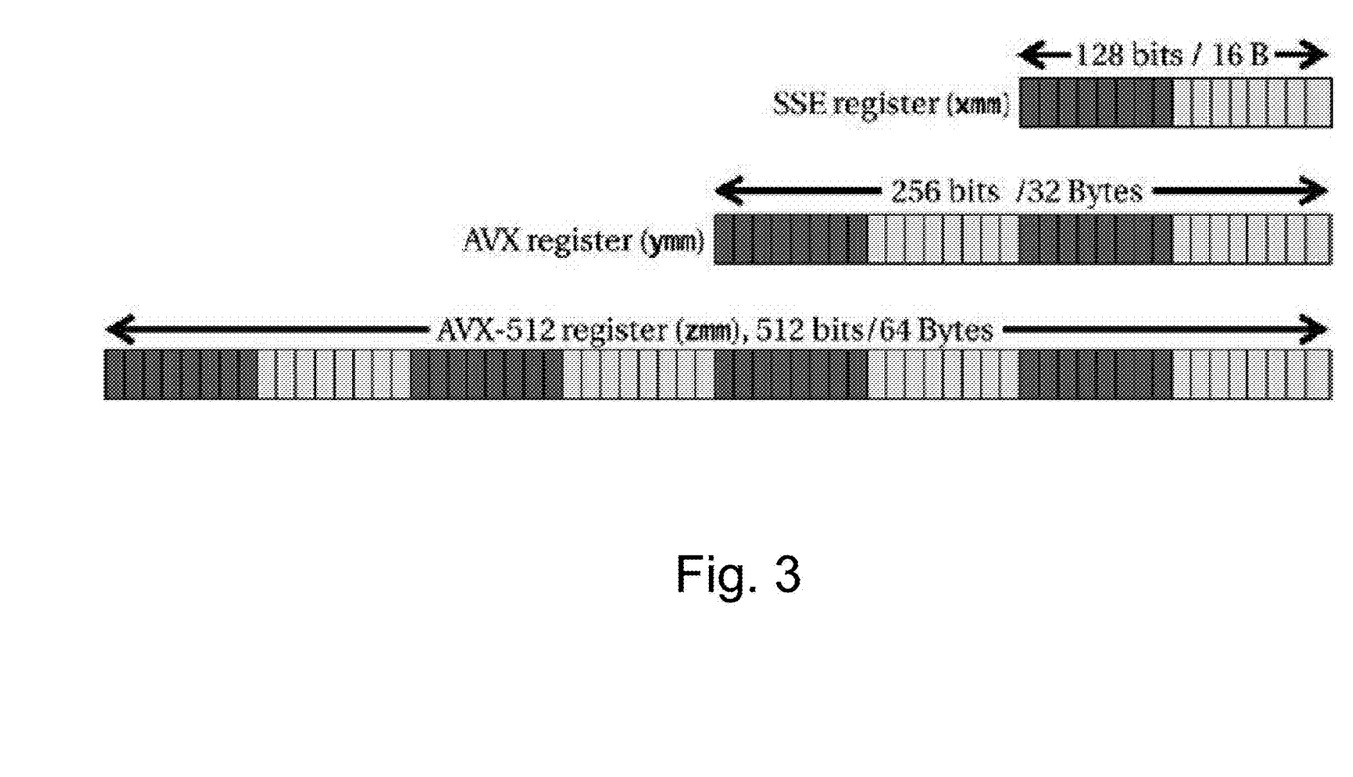
FIG. 3 shows optimal selection of keys to comply with the proposed SPHD method.

FIG. 3 shows optimal selection of keys to comply with the proposed SPHD method. A 512 bit register is used to load data in a single step, depending on the size of the basic element and the primary key size, while calculating how many steps are used for each register loading. For example, if the basic element is 5 bits and 20 bits are used for the primary key size, it will be required that the next register load shall be optimized and aligned to 8 bit. In this case, the calculation will be: int((512−20)/(5*8))=12, such that 12 steps will be used for each register.

In each step it is possible to rotate right using the basic element and get the lowest primary key value using 64 or 32 or 16 bit register with or without an AND arithmetic function, depending on the primary key value size. For example, if the primary key value size is 64 bit or 32 bit, 16 bit or 8 bit, only static_cast is required (in C++ type conversion, the static_cast operator performs an explicit type conversion).

The next 512 bit register will load the next value after 60 bytes. This is still more optimized considering the overall performance, even if 4 bytes got "lost" during comparison. the proposed SPHD method can be also implemented to 256 and 128 bit and also to greater register size like 1024, depending on the type of CPU used.

The method proposed by the present invention uses a condensed DNA file, which is created, based on gene Indexing (genes and mutations) with gene position and difference data (from the original gene). Unidentified areas will be stored for future use.

Figure 4:
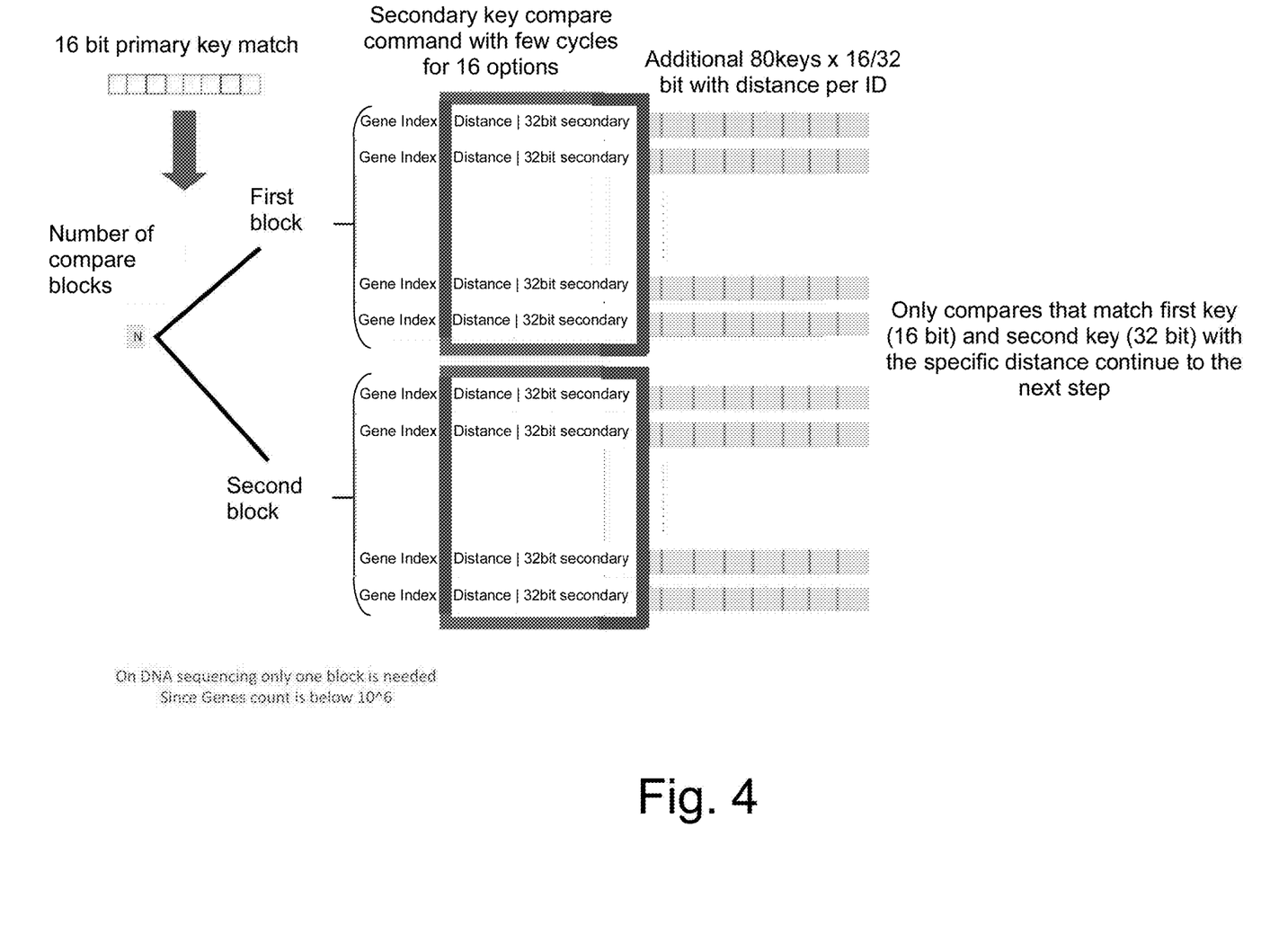
FIG. 4 illustrates the process of performing comparisons for several compare blocks in parallel, for gene indexing.

FIG. 4 illustrates the process of performing comparisons for several compare blocks in parallel, for gene indexing. After obtaining a match for a 16-bit primary key, a secondary key compare command is performed in parallel, on several blocks. In this example, each entry of a block comprises the gene index and the distance between the primary key and the secondary key, which is a 32 bit secondary key. Additional third multiple keys are of 16 or 32 bits with a corresponding distance for each gene ID. Comparisons are made in parallel on all blocks and only the comparisons that match the primary 16 bit key and the secondary 32 bit key with a predetermined distance between keys, are passed to the next stage. Only one block is needed for gene sequencing, since the genes count is smaller than $10^6$.

Figure 5:
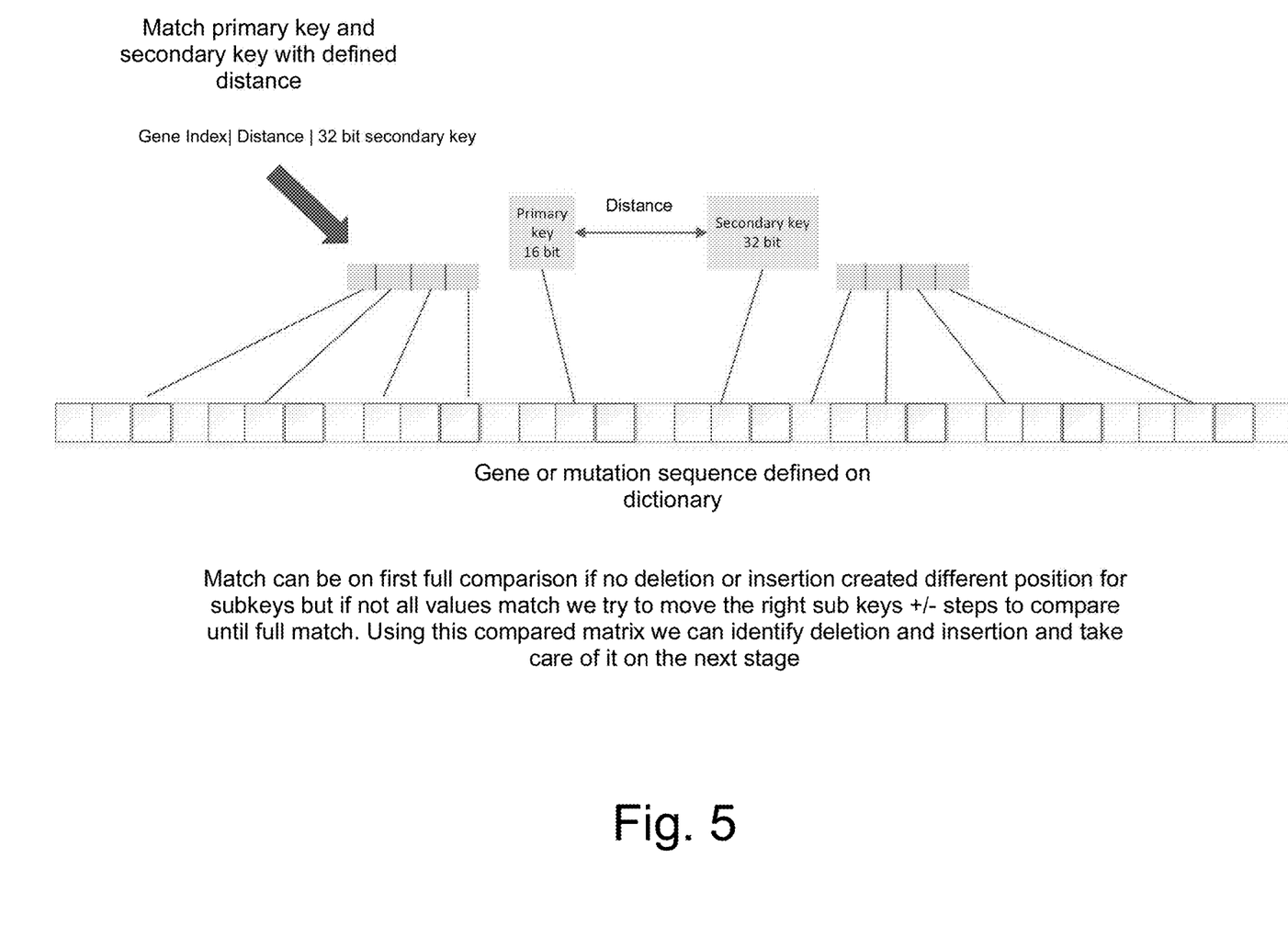
FIG. 5 illustrates the process of performing comparisons for several compare blocks in parallel, for rapidly identifying insertions and deletions.

FIG. 5 illustrates the process of performing comparisons for several compare blocks in parallel, for rapidly identifying insertions and deletions. Matching can be obtained on a first comparison if there are no deletions or insertions that entail different positions for subkeys (which are portions of the third multiple keys). If matching does not exist for all values, then the subkeys are moved to the right (+) and to the left (−) by a predetermined number of steps before performing further comparisons, until obtaining full match for both subkeys. Upon reaching a full match, it is possible to identify insertion, deletion and replacement operations that were made.

In NGS sequencing, for each partial DNA genes and mutation detections are performed, while similarity (including variants) is identified based on the detected "Blocks" (Genes and Mutations) and the order of those "Blocks" (a portion of the Genome sequencing part). It is possible to combine those partial DNA sequences into the original DNA sequence, based on the similarity.

The present invention allows full Genome sequencing, which is obtained by detecting all the "Blocks" (Genes and Mutations) on each sequence. A full Genome sequence can be merged, based on the blocks ID and distance between blocks and their known location on the DNA.

The following estimated performance on ARM A73 Quad core 2.2 Ghz CPU Power: 2.2 Ghz×4 Cores=8.8 Giga Cycles/Sec is illustrated:

Detected Gene process: 100,000 Genes and mutations×4 entries per Gene×200,000 Cycles (detecting suspected Gene and find the match)=80 Giga Cycles DNA Stream processing: 3,000,000,000 Basis×50 Cycles per Basis=150 Giga Cycles Total: 230 Giga Cycles/8.8 Giga Cycles Operating System (OS) Overhead: 15%

Estimated time performance for full Genome sequencing: 30 Sec

Figure 6A:
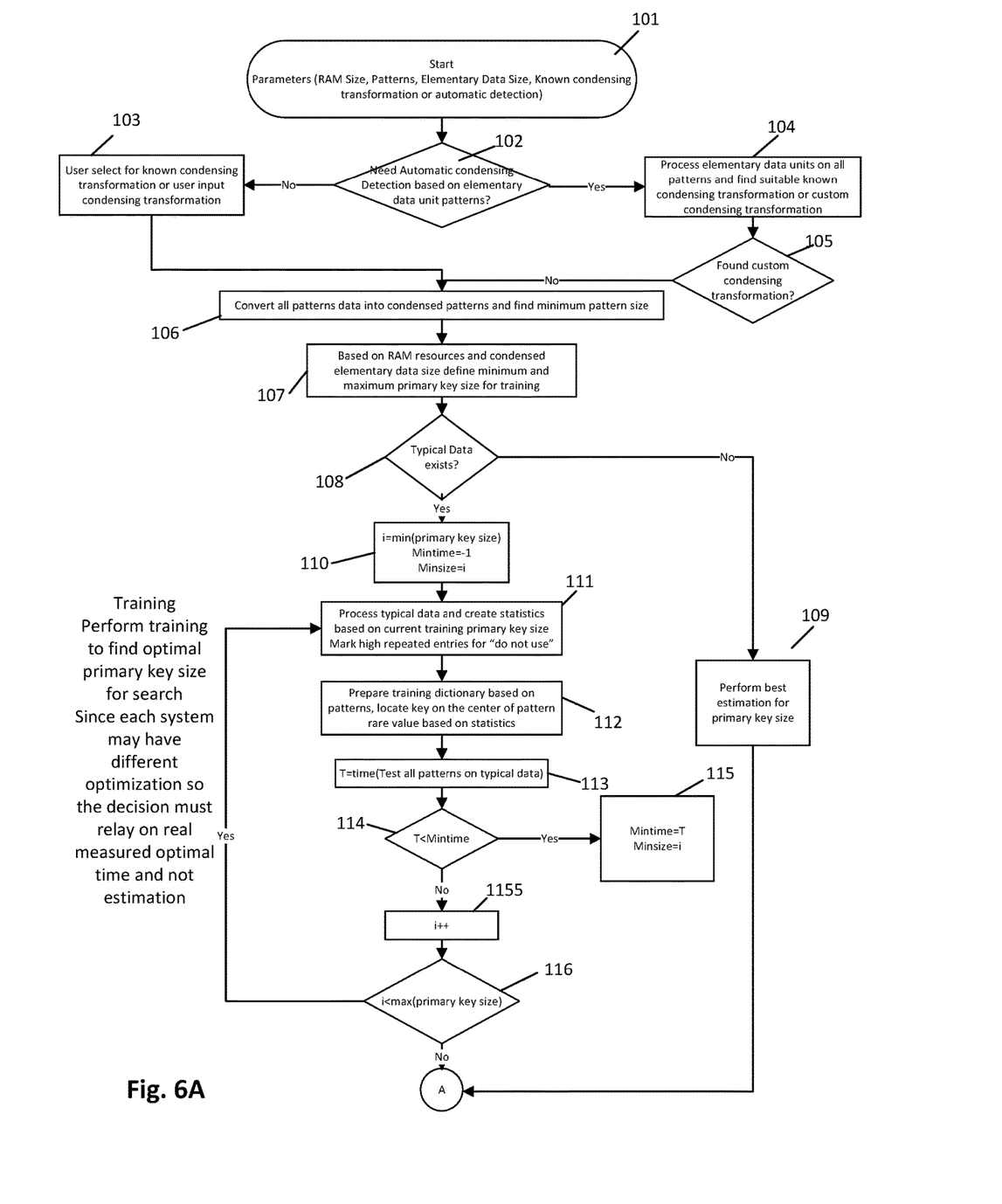
FIG. 6A is a flowchart of the process of defining the optimal search keys.

FIG. 6A is a flowchart of the process of defining the optimal search keys, according to an embodiment of the invention. At the first step 101, essential parameters such as RAM Size, Patterns, Elementary Data Size, condensing transformation (based on the conversion table) or automatic detection are defined. At the next step 102, the process checks whether or not Automatic condensing Detection based on elementary data unit patterns is required. If not, at the next step 103 the user selects known condensing transformation or inputs a new condensing transformation. If yes, at the next step 104, elementary data units on all patterns are processed and a suitable known condensing transformation or custom condensing transformation are found. At the next step 105, the process checks whether or not a custom condensing transformation is found. If not, at the next step 106, all patterns data is converted into condensed patterns and a minimum pattern size is found. At the next step 107, the minimum and maximum primary key size for training (the process of dictionary establishment), are defined, based on RAM resources and condensed elementary data size. At the next step 108, the process checks whether or not typical data (from the pre-processing stage) exists. If not, at the next step 109 the best estimation for primary key size is performed. If yes, at the next step 110 the minimal size of i=min(primary key size) where Min_time (the minimal time to test all pattern of typical data)=−1. At the next step 111, the typical data is processed and statistics is created, based on current training primary key size. Mark high repeated entries for "do not use". At the next step 112, a training dictionary is prepared, based on patterns, and a key is located on the center of the pattern's rare value, based on statistics. At the next step 113, all patterns are tested on typical data. At the next step 114, the process checks whether or not T<Min_time. If yes, at the next step 115 the process sets the time T required to test all the pattern on typical data) to be T=Min_time and Mn_Size (Minimum pattern Size)=i. At the next step, i is incremented to i++. At the next step 116, the process checks whether or not i<max(primary key size). If yes, the process goes to step 111. Otherwise, at the next step 117, the process decides what will be the secondary key size and the multiple key sizes, depending on fixed accurate data area size and fragmentation of patterns.

Figure 6B:
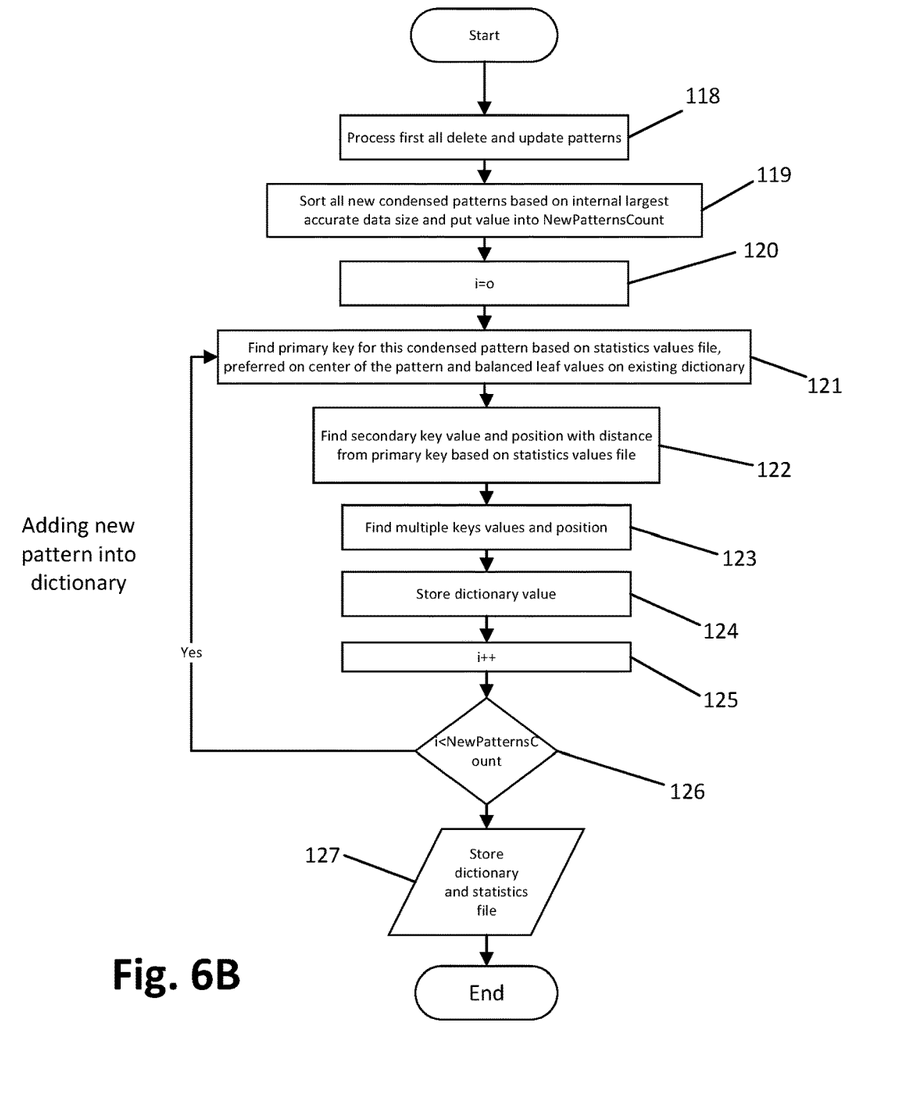
FIG. 6B is a flowchart of the process of defining the optimal dictionary.

FIG. 6B is a flowchart of the process of defining the optimal dictionary. At the first step 118, all "delete" and "update" patterns are processed first. At the next step 119, all new condensed patterns are sorted, based on the internal largest accurate data size and a value is inserted into NewPatternsCount (a function that counts the number of new patterns). At the next step 120, i is set to be zero (i=0). At the next step 121, a primary key is found for this condensed pattern, based on a statistics values file. Preferred values are on the center of the pattern and balanced leaf values on existing dictionary. At the next step 122, a secondary key value and position with distance from primary key are found, based on the statistics values file. At the next step 123, multiple keys values and positions are found. At the next step 124, the dictionary values are stored. At the next step 125, i is incremented to i++. At the next step 126, the process checks whether or not i<NewPatternsCount. If yes, the process goes to step 121. Otherwise, at the next step 127 the dictionary and the statistics file are stored.

Figure 7:
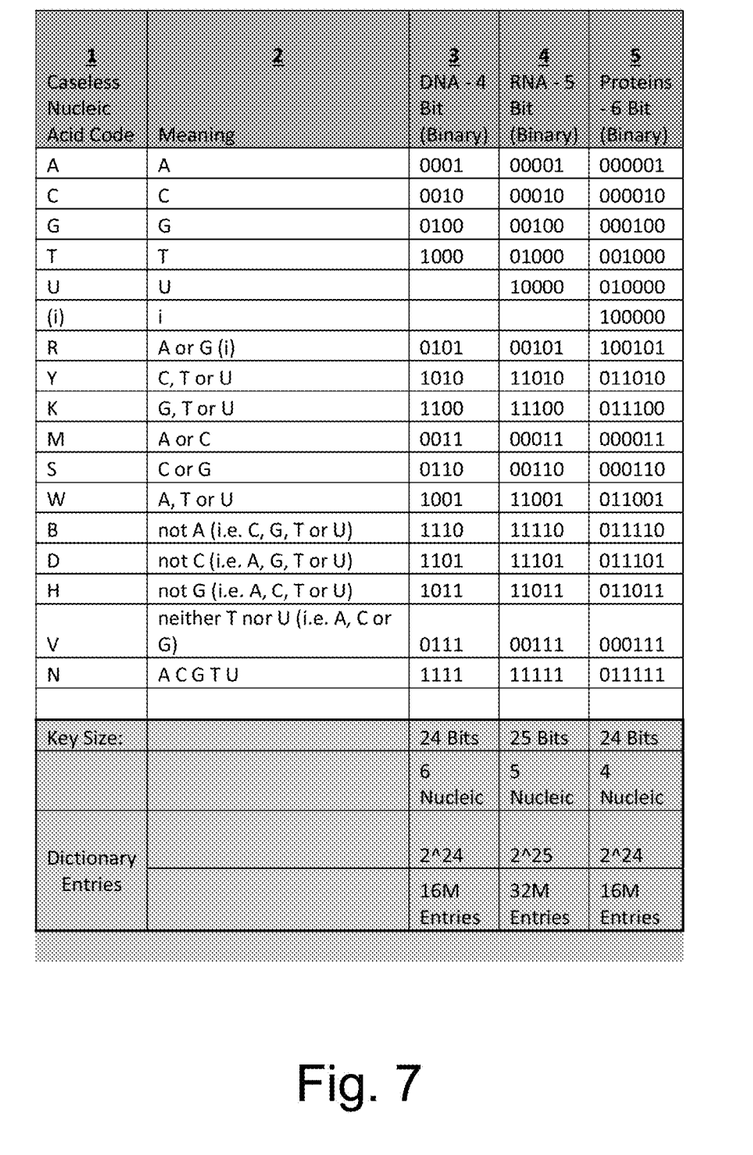
FIG. 7 illustrated a table of searchable acid codes on DNA, RNA and other (more complicated) proteins, according to another embodiment.

FIG. 7 illustrated a table of searchable acid codes on DNA, RNA and other (more complicated) proteins, according to another embodiment. As long as the pattern are DNA patterns, they are represented using 4 bits (acid codes A, C, G, T), as shown in column 3. RNA patterns are represented by acid code R (A or G), where the bits of A and G are activated, as shown in column 4. U and i do not exist in DNA and i does not exist in RNA. The patterns of other proteins are represented using 6 bits, as shown in column 5. In this case, the size of the dictionary is not established on the fly (according to the types of patterns), but is established in advance and has a constant size. This allows performing the comparisons using a simple AND operation, to thereby reduce the processing time. If the AND operation result for each elementary value is greater than 0, the compared patterns are equal. In case of cyber-attacks, the patterns are represented by 8 bits. Using a fixed number of bits for representing elementary units in the dictionary reduces the chance that a key will be repetitive.

The above examples and description have of course been provided only for the purpose of illustrations, and are not intended to limit the invention in any way. As will be appreciated by the skilled person, the invention can be carried out in a great variety of ways, employing more than one technique from those described above, all without exceeding the scope of the invention.

The invention claimed is:

1. A method for performing fast data pattern searches, comprising:
   creating, based on data patterns or based on known elementary unit data, elementary units that are condensed by performing a conversion;
   automatically creating, by a computerized device, an indexed dictionary containing the data patterns to be searched;
   selecting, by the computerized device, a primary key for each searched data pattern of the searched data patterns using statistics and secondary keys counting on a primary key value of the primary key,
   wherein the indexed dictionary has entries that are balanced over all entries of an array based on numbers of the secondary keys,
   for said each searched data pattern of the searched data patterns, selecting, by the computerized device, a primary key to search for a first fragment of the searched data pattern to be compared;
   automatically creating, by a computerized device, a secondary key to search for a second fragment of said each searched data pattern of the searched data patterns, wherein the secondary key is greater than a size of the primary key to both directions, the secondary key functions as a filtering element, where only entries that have a match in a secondary key value of the secondary key and a corresponding distance will move to a next processing stage as a training stage;
   preforming, by the computerized device, the training stage to obtain a fastest optimal combination on the primary key size and a secondary key size;
   processing, based on the condensed elementary units and based on the preforming the training stage, typical search data to gather statistics regarding a probability of identifying the searched data patterns, wherein the processing of the typical search data includes revoking entries options that are used multiple times from the entries according to a predetermined threshold;
   automatically creating, by the computerized device, third multiple keys for multiple fragments of said each searched data pattern to be compared to determine matches;
   performing, by the computerized device, full comparisons between words in the indexed dictionary and segments of streamed or stored data in response to determined matches; and
   obtaining, by the computerized device based on the performing the full comparisons, a final result after performing partial searches consisting of a combination of partial accurate and inaccurate searches to filter out entry values that are not possible, wherein the final result includes values from the indexed dictionary,
   wherein the corresponding distance of the secondary key before or after the primary key is predetermined and wherein each entry of the array defines multiple entries to be compared as the secondary keys, wherein each secondary key of the secondary keys has a unique distance defined from the primary key.

2. The method according to claim 1, wherein a full identified pattern is obtained, thereby supporting a combination of versatile patterns consisting of small patterns.

3. The method according to claim 2, wherein the small patterns range from two elementary units up to condensed pattern size of two Gigabytes on a same dictionary.

4. The method according to claim 1, wherein the elementary unit data includes one of: DNA data; numbers; or strings.

5. The method according to claim 1, wherein the threshold is entries options that are used more than double times from other entries.

6. The method according to claim 1, wherein the searched data is effectively cached data.

7. The method according to claim 1, wherein entry values that are used more often are deliberately revoked by pre-processing typical data.

8. The method according to claim 1, wherein the indexed dictionary contains only entries that were not revoked or values that do not exists.

9. The method according to claim 1, wherein the indexed dictionary is adapted to: add new entries; update existing entries; and delete existing entries.

10. The method according to claim 1, wherein whenever there is an insertion of a gene or mutation, said insertion is directed to an input in the array that has been minimally used.

11. The method according to claim 1, wherein the indexed dictionary includes one or more of:
- a collection of all genes and known mutations for humans, animals, plants, viruses, bacteria and fungus;
- circulating free DeoxyriboNucleic Acid (DNA) (cfDNA—degraded DNA fragments released to blood plasma);
- full genomes sequence for existing life including humans, animals, plants, viruses, bacteria and fungus.

12. The method according to claim 1, wherein small fragmented definite areas within a pattern reduce a key size.

13. The method according to claim 1, wherein the secondary key is located near the primary key.

14. The method according to claim 1, wherein the secondary key and the corresponding distance from primary key function as filtering elements, such that only entries that have a match in the secondary key value and the corresponding distance will move forward to the next stage.

15. The method according to claim 1, wherein whenever all keys and distances are larger than value size of a register for storing a history of the elementary units, bit size will include several values for each key.

16. The method according to claim 1, wherein each array entry has multiple entries that comply the primary key, to be compared as secondary keys.

17. The method according to claim 1, wherein the primary key and the secondary key with a distance between the primary key and the secondary key are being accurate for an inaccurate search.

18. The method according to claim 1, wherein a type of entries includes: entry values that are not possible; entry values that are used more often; and entry values with multiple secondary keys with unique distance.

19. The method according to claim 1, wherein a size of the indexed dictionary is established in advance and the indexed dictionary has a constant size, for allowing performing comparisons using an AND operation, to thereby reduce processing time.

20. The method according to claim 1, wherein for cyber-attacks dictionary, the elementary units in patterns from the indexed dictionary are represented by eight bits, to reduce a chance that one or more keys will be repetitive.

21. The method of claim 1 wherein the elementary units are created automatically.

22. A system for performing fast data pattern searches, comprising:
- a computerized device consisting of at least one processor and a memory coupled to the processor, the computerized device being configured to:
  - create, based on data patterns or based on known elementary unit data, elementary units that are condensed by performing a conversion;
  - automatically create an indexed dictionary containing the data patterns to be searched;
  - select a primary key for each searched data pattern of the searched data patterns using statistics and secondary keys counting on a primary key value of the primary key,
  - wherein the indexed dictionary has entries that are balanced over all array entries of an array based on numbers of the secondary keys,
  - for said each searched data pattern of the searched data patterns, select a primary key to search for a first fragment of the searched data pattern to be compared;
  - automatically create a secondary key to search for a second fragment of said each searched data pattern of the searched data patterns, wherein the secondary key is greater than a size of the primary key to both directions, the secondary key functions as a filtering element, wherein only entries that have a match in a secondary key value of the secondary key and a corresponding distance of the secondary key will move to a next processing stage as a training stage;
  - preform the training stage to obtain a fastest optimal combination on the primary key size and a secondary key size;
  - process, based on the condensed elementary units and the preforming the training stage, typical search data to gather statistics regarding a probability of identifying the searched data patterns, wherein the processing of the typical search data includes revoking entries options that are used multiple times from the entries according to a predetermined threshold;
  - automatically create third multiple keys for multiple fragments of the searched data pattern to be compared to determine matches;
  - perform full comparisons between words in the indexed dictionary and segments of streamed or stored data in response to there were the matches; and
  - obtain, based on the performing the full comparisons, a final result after performing partial searches consisting of a combination of partial accurate and inaccurate searches to filter out entry values that are not possible, wherein the final result includes values from the indexed dictionary,
  - wherein the corresponding distance of the secondary key before or after the primary key is predetermined, wherein each entry of the array defines multiple entries to be compared as the secondary keys, wherein each secondary key of the secondary keys has an unique distance defined from the primary key.

23. The system according to claim 22, wherein a full identified pattern is obtained, thereby supporting a combination of versatile patterns consisting of small patterns.

24. The system according to claim 23, wherein the small patterns range from 2 two elementary units up to condensed pattern size of two Gigabytes on a same dictionary.

25. The system according to claim 22, wherein the elementary unit data includes one of: DeoxyriboNucleic Acid (DNA) data; numbers; or strings.

26. The system according to claim 22, wherein the threshold is entries options that are used more than double times from other entries.

27. The system according to claim 22, the searched data is effectively cached data.

28. The system according to claim 22, wherein full comparisons to obtain the final result are made after performing partial searches consisting of a combination of partial accurate and inaccurate searches, thereby filtering out entry values that are not possible.

29. The system according to claim 22, wherein entry values that are used more often are deliberately revoked by pre-processing typical data.

30. The system according to claim 22, wherein the indexed dictionary contains only entries that were not revoked or values that do not exists.

31. The system according to claim 22, wherein the indexed dictionary is adapted to: add new entries; update existing entries; and delete existing entries.

32. The system according to claim 22, whenever there is an insertion of a gene or mutation, said insertion is directed to an input in the array that has been minimally used.

33. The system according to claim 22, wherein the indexed dictionary includes one or more of:
- a collection of all genes and known mutations for humans, animals, plants, viruses, bacteria and fungus,
- circulating free DeoxyriboNucleic Acid (DNA) (cfDNA—degraded DNA fragments released to the blood plasma); or
- full genomes sequence for existing life including humans, animals, plants, viruses, bacteria and fungus.

34. The system according to claim 22, wherein small fragmented definite areas within a pattern reduce a key size.

35. The system according to claim 22, wherein the secondary key is located near the primary key.

36. The system according to claim 22, wherein the secondary key and the corresponding distance from primary key function as filtering elements such that only entries that have a match in the secondary key value and the corresponding distance will move forward to the next stage.

37. The system according to claim 22, whenever all the secondary keys and distances are larger than a value size of a register for storing a history of the elementary units, a bit size will include several values for each key.

38. The system according to claim 22, each array entry has multiple entries that comply the primary key, to be compared as secondary keys.

39. The system according to claim 22, wherein the primary key and the secondary key with a distance between the primary key and the secondary key are being accurate for an inaccurate search.

40. The system according to claim 22, wherein a type of entries includes: entry values that are not possible; entry values that are used more often; entry values with multiple secondary keys; and entry values with unique distance.

41. The system of claim 22 wherein elementary units are created automatically.

* * * * *

UNITED STATES PATENT AND TRADEMARK OFFICE
CERTIFICATE OF CORRECTION

PATENT NO. : 12,099,554 B2
APPLICATION NO. : 18/477849
DATED : September 24, 2024
INVENTOR(S) : Israel Zimmerman Page 1 of 1

It is certified that error appears in the above-identified patent and that said Letters Patent is hereby corrected as shown below:

In the Claims

In Column 15, in Claim 16, Line 42, delete "key," and insert -- key --, therefor.

In Column 16, in Claim 22, Line 13, before "numbers" insert -- the --.

In Column 16, in Claim 22, Line 20, before "greater" delete "is".

In Column 16, in Claim 22, Line 22, delete "wherein" and insert -- where --, therefor.

In Column 16, in Claim 22, Line 23, after "and" delete "a" and insert -- the --, therefor.

In Column 16, in Claim 22, Line 25, before "next" delete "a" and insert -- the --, therefor.

In Column 16, in Claim 22, Line 29, after "based on" delete "the".

In Column 16, in Claim 22, Line 29, after "and" delete "the".

In Column 16, in Claim 22, Line 37, delete "pattern" and insert -- pattern, --, therefor.

In Column 16, in Claim 22, Line 51, after "as" delete "the".

In Column 16, in Claim 24, Line 58, after "from" delete "2".

In Column 18, in Claim 38, Line 15, delete "key," and insert -- key --, therefor.

Signed and Sealed this
Eleventh Day of February, 2025

Coke Morgan Stewart
*Acting Director of the United States Patent and Trademark Office*